US006730917B2

United States Patent
Baggett et al.

(10) Patent No.: US 6,730,917 B2
(45) Date of Patent: May 4, 2004

(54) MINIATURE HIGH INTENSITY LED ILLUMINATION SOURCE

(75) Inventors: Ray Baggett, Panama City Beach, FL (US); Billy Courson, Panama City Beach, FL (US); Pete Sagasti, Oceanside, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 169 days.

(21) Appl. No.: 10/042,856

(22) Filed: Jan. 11, 2002

(65) Prior Publication Data

US 2003/0131941 A1 Jul. 17, 2003

(51) Int. Cl.⁷ .............................................. B25B 33/00
(52) U.S. Cl. .............................. 250/453.11; 250/453.11; 250/454.11; 250/455.11; 433/29; 433/80; 433/215; 433/229; 315/224
(58) Field of Search ................................ 250/492.1, 504, 250/453.11, 454.11, 455.11, 461.1, 458.1, 159.1; 433/29, 80, 215, 229; 362/231

(56) References Cited

U.S. PATENT DOCUMENTS 5,634,711 A * 6/1997 Kennedy et al. ............. 362/119

* cited by examiner

Primary Examiner—John R. Lee
Assistant Examiner—David A. Vanore
(74) Attorney, Agent, or Firm—Donald G. Peck; Harvey A. Gilbert

(57) ABSTRACT

An apparatus emits radiation on curable adhesives to bond objects or surfaces together under a variety of ambient conditions. An insulating housing has a cylindrical section and a disc-shaped section defining an interior. A plurality of batteries and an LED array are separated in the interior by an insulating spacer to prevent shorting of the batteries. A switch relay in the interior connects power from the batteries to the LED array when a switching mechanism mounted on the outside of the housing is displaced. This displacement closes the switch relay and connects power to the LED array that emits high-intensity radiation. A cover connected to the cylindrical-shaped section seals the interior from ambient and transmits the high-intensity radiation to cure an adhesive.

9 Claims, 1 Drawing Sheet

MINIATURE HIGH INTENSITY LED ILLUMINATION SOURCE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to devices for curing adhesives to bond objects together. In particular, this invention relates to a device adapted for radiating light onto photo-curable adhesives in different ambient conditions.

Adhesive compounds have been developed that initiate curing when they are radiated by light from an electric lamp. The curing light may be not only visible light, but also other wavelengths, such as ultraviolet or infrared. Typically, two part reactive adhesives (epoxies, etc) are temperature dependent and cure sluggishly or not at all in the cold temperatures found in seawater. These cold water conditions also are extreme for divers, and little time can be afforded to wait on adhesive to cure in a remote application. Divers do not have an acceptable quick bonding adhesive system in demanding underwater applications where speed of curing is effective throughout the range of seawater conditions (90° F.–29.5° F.).

Thus, in accordance with this inventive concept, a need has been recognized in the state of the art for a user friendly bonding system that can be transported, operated, and applied to cure bonding adhesive quickly in extreme conditions.

SUMMARY OF THE INVENTION

An object of the invention is to provide a compact, user-friendly system to cure photo-curable adhesives with light.

Another object of the invention is to provide a user-friendly system to bond objects underwater or in air under adverse conditions.

Another object of the invention is to provide a portable, miniature system utilizing a high powered illumination source for curing photo-curable adhesives underwater and in-air.

Another object of the invention is to provide a safe, user-friendly system to cure adhesives and operable underwater by heavily gloved hands.

Another object of the invention is to provide a portable, miniature system utilizing a high powered LED illumination source for curing photo-curable adhesives underwater and in-air and additionally can be used as a high intensity LED lamp.

Another object of the invention is to provide a user-friendly device transported to and operated at a work site to cure a bonding adhesive quickly in extreme conditions.

These and other objects of the invention will become more readily apparent from the ensuing specification when taken in conjunction with the appended claims.

Accordingly, the invention provides an apparatus for curing an adhesive with high-intensity radiation. A housing has an insulating cylindrical section and disc-shaped section to define an interior. An LED array in the housing is separated from batteries by an insulating layer. A switching mechanism mounted on the outside of the housing is displaced to close contacts of a switch relay in the housing to connect power from the batteries to the LED array. The LED array emits the high-intensity radiation through a transparent cover to cure an adhesive.

DESCRIPTION OF THE PREFERRED EMBODIMENTS

Figure 1:
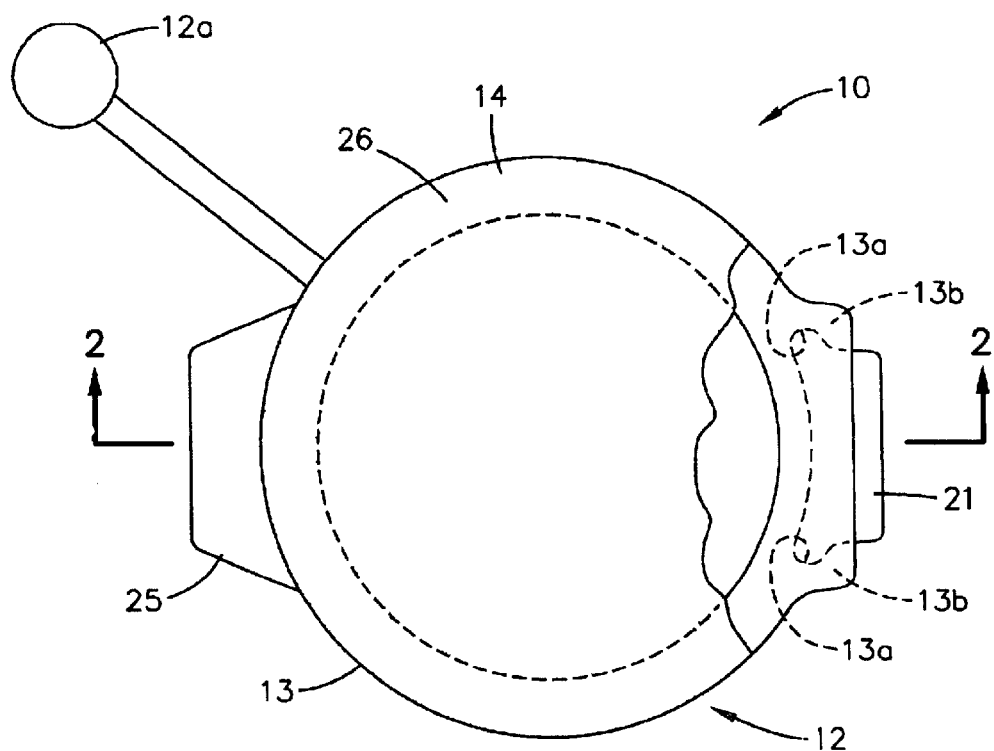
FIG. 1 is a top view of the illumination source of the invention.
Figure 2:
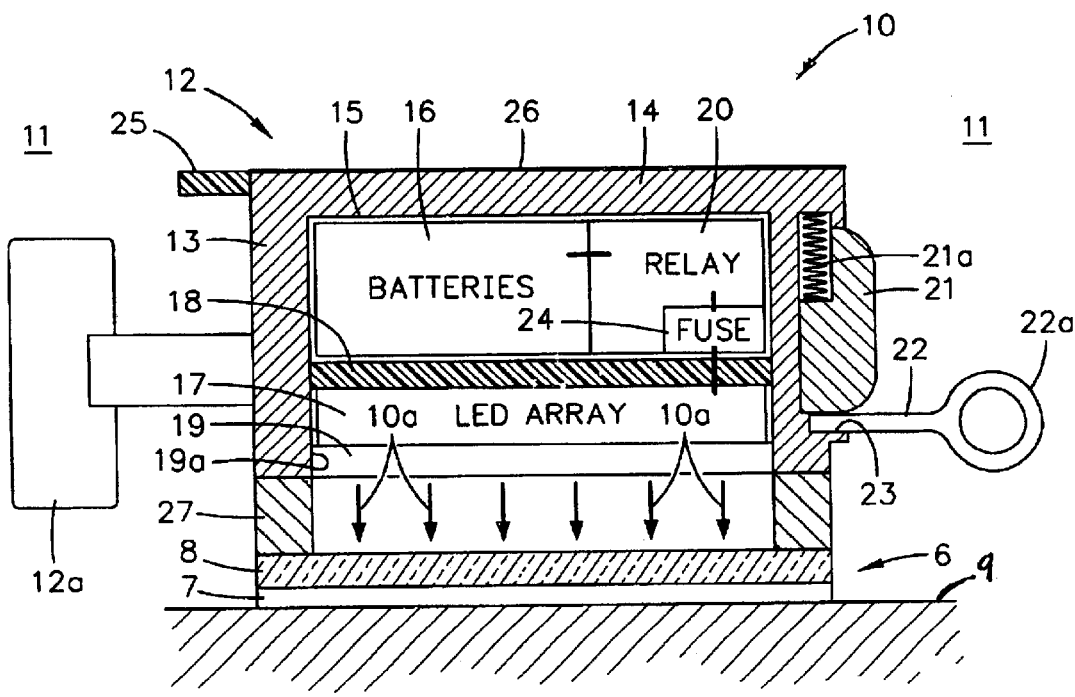
FIG. 2 is a cross-sectional side view of the illumination source of this invention taken generally along line 2—2 in FIG. 1 and showing bonding of a photo-curable adhesive after being transported to and placed on a submerged surface.

Referring to FIGS. 1 and 2 of the drawings, illumination source 10 provides a miniature, high-powered source of energy for curing photo-curable adhesives in different underwater and in-air applications, such as in ambient water 11. Illumination source 10 is intended to include those sources of radiation that may be used to cure adhesives including photo-activated adhesives. Illumination source 10 is compact enough to be easily transported to work-site 6 by a workman, and is ergonomically designed for use by an operator wearing heavy gloves. It reliably operates over temperature ranges between 90° F.–29.5° F. underwater and over ambient temperatures in air or other places where curing of adhesives is needed to bond surfaces and/or objects together.

FIG. 2 depicts illumination source 10 adjacent work site 6 that has an envelope of photo-curable adhesive 7 between a radiation transparent structural member 8 and submerged slab 9. Member 8 is being bonded to submerged slab 9 as high intensity radiation 10a from source 10 is being emitted. The properties of adhesive 7 are such as to be cured by the emitted high-intensity radiation 10a in not only this exemplary arrangement of adhesive 7, member 8 and surface 9, but other arrangements as well. This is due to the high levels of radiation 10a emitted by source 10 and also due to the compact design of source 10 which allows proximity to work site 6.

Source 10 has an essentially can-shaped housing 12 including a cylindrical-shaped section 13 and a disc-shaped section 14. Sections 13 and 14 of housing 12 can be cast, machined, or otherwise appropriately fashioned from a variety of suitably workable strong materials, such as urethane, plastic compounds, etc. Metals can be used for housing 12 so long as electrical insulation is provided for components contained in them. The sections can be made as an integral unit or securely interconnected and sealed together to provide an interior 15 that is watertight, electrically insulating, and/or otherwise protected from the ambient.

A plurality of batteries 16 is held in interior 15 as a source of power for an array of light emitting diodes (LED's) 17. Batteries 16 can be high-energy lithium batteries electrically insulated from ambient water 11 via housing 10, and batteries 16 are separated from LED array 17 by an insulating spacer layer 18. Insulating spacer layer 18 helps prevent the possibility of shorting the high-energy batteries as source 10 is subjected to the routine abuses expected underwater.

A disc-shaped, clear acrylic cover 19 to transmit radiation from LED array 17 extends across cylindrical-shaped section 13 of housing 12 and is connected to section 13 via an adhesive sealant 19a. Adhesive sealant 19a seals interior 15 from ambient 11.

Cover 19 can have a suitable optical coating 19b on either side to function as a "one-way" mirror so that radiation from LED array 17 can only travel out of radiation source 10. This may reduce optical losses that might otherwise be due to the absorption of reflective waves. Optical coating 19b may also be a film that permits only one-way travel of radiation from radiation source 10. Furthermore, optical coating 19b, or the face of cover 19 can be modified to have light filtering characteristics. Optionally, many different types of optical filters might be incorporated in cover 19 and coating 19b and additional filters may be added on depending on the application.

Batteries 16 are located in interior 15 on top of spacer layer 18 and LED array 17. Batteries 16 can be any of a variety of off-the-shelf packs of high-power batteries from several different manufactures to provide enough power over a sufficient period of time to allow LED array 17 to emit enough radiation through cover 19 to cure a photo-curable or other radiation curable adhesive. For example, batteries can be six, 3-volt lithium, size 123 batteries, such as the model CR123A batteries marketed by Panasonic. The lithium 123 batteries have shown a ten-year shelf life and have high power density. Optical output from LED array 17 of source 10 decreases from a peak initial value as electrical power is drained from batteries 16. This peak has been measured to be approximately 24 mw/cm2, and appears to cause an adhesive to be adequately cured within 15 seconds.

LED array 17 can be a suitable number of light emitting diodes or other high-intensity sources wired in two concentric sections. Diodes of LED array 17 can be operated together or focused in many different ways or be arranged in banks of variable numbers of LED's that can emit sufficient amounts of 470 nm (blue) peak. This emission cures photo-curable adhesives that are responsive to such emission to be cured. Other photo-curable adhesives responsive to other emissions could have been used provided the selected LED's emitted sufficient radiation at the right wavelengths to effect curing of the other adhesives. Accordingly, many other off-the-shelf LED's having other spectral emissions may be selected and used to cure other adhesives that are compatible to be cured by the emissions from the other LED's. The emissions referred to herein are intended to embrace electromagnetic radiation from LED's that could be utilized to energize the photo initiator in the selected radiation-curable adhesives and may include, but are not limited to include any or all of infrared light, visible light, or ultraviolet light. Although source 10 is designed to cure adhesives, it can be used in other applications where high intensity LED light is required.

Furthermore, in accordance with this inventive concept, illumination source 10 includes a switch relay 20 in interior 15 that is actuated to connect electrical power from batteries 16 to LED array 17. Switch relay 20 can have magnetically influenced reed contact structures (not shown) that are selectably displaced to close the reed contact structures and establish an electrical connection between batteries 16 and LED array 17 when a magnetic switching mechanism 21 is appropriately displaced on housing 12. In the alternative, the contact structures could be opened to effect some other interconnection scheme that gets power from batteries 16 to LED array 17, if desired.

Magnetic switching mechanism 21 does not penetrate housing 12 and can be a magnet sized to slideably fit within a groove 13a between two longitudinal projections 13b on cylindrical-shaped section 13 of housing 12. Magnetic switching mechanism 21 is large enough to be engaged by a gloved operator to permit its longitudinal displacement in groove 13a. Magnetic switching mechanism 21 is shown at the upper, or "off" position in FIG. 2, and in this "off" position the magnetically influenced reed contacts of switch relay 20 are in the open position and do not connect power from batteries 16 to LED array 17.

A safety pin 22, optionally may be retained in a hole 23 provided in the lower end of cylindrical-shaped section 13 to prevent inadvertent displacement of magnetic switching mechanism 21 and actuation of LED array 17. After the operator pulls safety pin 22 from hole 23 via an interconnected pull-ring 22a, magnetic switching mechanism 21 is free to be displaced from the "off" position.

The operator moves magnetic switching mechanism 21 to the lower, or "on" position at the lower end of housing 12 next to cover 19. The magnetic influence of the magnet of magnetic switching mechanism 21 closes reed contact structure of switch relay 20 and establishes an electrical connection between batteries 16 and LED array 17. Electrical power from batteries 16 is connected to LED array 17, and high-intensity radiation is emitted from LED array 17 through cover 19 and onto a radiation (photo)-curable adhesive. Magnetic switching mechanism 21 can also have a spring 21a connected to housing 12 that biases it to the "off" position. An operator must overcome the biasing force to displace magnetic switching mechanism 21 to the "on" position. If mechanism 21 is released, LED array 17 automatically turns off. As an alternative, this feature can be changed such that LED array 17 stays "on" when the switch is released.

A fuse 24 can be provided in interior 15 of housing 12 and be coupled between batteries 16 and LED array 17 to prevent a hazardous condition that might occur, for example, if an overload current is created. Such overload current might by caused by an electrical short that might somehow be created in the circuit including high-energy lithium batteries 16. If fuse 24 were not included to break the circuit, damage to source 10 and/or injury to operator might otherwise result from a possible high-energy surge of current from batteries 16.

Housing 12 can have a blade section 25 co-extending from disc-shaped section 14. Blade section 25 can be made from metal or other hard material that may be used to scrape-away matter during preparation of a surface. Housing 12 can also have an abrasive sandpaper-like or wire brush-like layer 26 on disc-shaped section 14. An operator can rub layer 26 back and forth on a surface to be clean it prior to applying an adhesive and curing it with radiation from source 10. Optionally, layer 26 can be sponge-like and contain a chemical that "eats away" surface contaminates when an operator applies it to them.

Illumination source 10 can have a compliant rubber boot, or annular shroud 27 co-extending from cylindrical-shaped section 13 around the periphery of cover 19. Shroud 27 is compliant to accommodate the surface around an area receiving radiation from illumination source 10. This will confine the transmission of high-intensity radiation to the adhesive and prevent the transmission of any part of the radiation to ambient 11 beyond work site 6.

Illumination source 10 of the invention 10 is a high output small, portable, and lightweight source that can measure about four inches in diameter and about two inches high. Its compact size permits it to be carried by an operator in a pouch or by a lanyard, and its ergonomic design permits user-friendly tactile operation by a heavily gloved diver. Source 10 may have different buoyancy characteristics, and for the present intended underwater application, slight negative buoyancy is preferred. Source 10 may be of different colors that are easily, or not easily seen and may have a handle 12*a* to help placement.

In accordance with this invention illumination source 10 is a cost effective and expendable means to assure bonding by photo-curable adhesives. In addition illumination system 10 can be used as a source of illumination where a high-intensity source of radiation is needed. The size and geometry of housing 12 and cover 19 of illumination source 10 can be modified as needed and may be used in conjunction with a number of other like illumination sources 10 for increased levels of radiation.

Different actuation schemes other than switch relay 20 and switching mechanism 21 may be selected, e.g. acoustic or electrical actuation schemes. A wide variety of strong corrosion resistant materials may be chosen for fabrication of the constituents of housing 12 and compliant shroud 27. Different sizes and amounts of batteries 16 may be chosen to vary the magnitudes of single or multiple uses and duration of each use. The number, color, wiring, and configuration of LED array 17 may be different in accordance with the task at hand. Gas or moisture absorbing material may be added to interior 15, and different internal structural arrangements might be selected. Optionally, illumination source 10 may include prepackaged photo-curable adhesive adjacent cover 19 and have mounting structure such as eyes, projections, etc. for attaching things to it.

The disclosed components and their arrangements as disclosed herein, all contribute to the novel features of this invention. These novel features of illumination source 10 assure more reliable and effective initiation and curing of photo-curable adhesives and bonding of objects together. Therefore, within the scope of this inventive concept illumination source 10 may be differently shaped and can be tailored to accommodate differently shaped surfaces for different tasks. Consequently, having this disclosure in mind, one skilled in the art to which this invention pertains will select and assemble components for illumination source 10 from among a wide variety available in the art. Therefore, the disclosed arrangement is not to be construed as limiting, but rather, is intended to be demonstrative of this inventive concept.

It should be readily understood that many modifications and variations of the present invention are possible within the purview of the claimed invention. It is to be understood that within the scope of the appended claims the invention may be practiced otherwise than as specifically described.

What is claimed is:

1. An apparatus for curing an adhesive with high-intensity radiation comprising:

a housing having an insulating cylindrical section and an insulating disc-shaped section defining an interior;

an LED array in said interior of said housing to emit high-intensity radiation;

a plurality of batteries in said interior of said housing adjacent said LED array to supply power to said LED array;

an insulating spacer layer interposed between said LED array and said plurality of batteries to prevent shorting of said batteries;

a switch relay in said interior of said housing connected to said LED array and said plurality of batteries;

a disc-shaped cover transparent to said high-intensity radiation and being disposed adjacent said LED array, said cover being connected to said cylindrical-shaped section to seal said interior from ambient;

a switching mechanism mounted on the outside of said housing, said switching mechanism being displaced on said housing to close said switch relay and connect said power to said LED array to emit said high-intensity radiation through said cover;

a fuse connected between said switch relay and said LED array to prevent overload current; and a safety pin to engage said housing and said switching mechanism together to prevent displacement of said switching mechanism.

2. An apparatus according to claim 1 further comprising:

a biasing spring connected to said housing and said switching mechanism to hold said switching mechanism in the off position.

3. An apparatus according to claim 2 further comprising:

a compliant shroud around said disc-shaped cover to prevent the transmission of said high-intensity radiation to the ambient.

4. An apparatus according to claim 3 wherein said LED array emits radiation at 470 nm.

5. An apparatus according to claim 4 further comprising:

an abrasive layer on said housing; and a blade section on said housing, said abrasive layer and said blade section being displaced to prepare a surface.

6. An apparatus according to claim 5 wherein said switching mechanism has a magnet sized to slideably fit within a groove on said cylindrical-shaped section of said housing to be engaged by a gloved operator to permit its longitudinal displacement said groove.

7. An apparatus according to claim 6 wherein said housing is about four inches in diameter and two inches high to permit user-friendly tactile operation.

8. An apparatus according to claim 7 wherein said cover has a coating to provide a one-way capability for emitted radiation.

9. An apparatus according to claim 6 wherein said cover has a coating to provide for filtering.

* * * * *